United States Patent [19]

Kozuma et al.

[11] Patent Number: 4,631,301

[45] Date of Patent: Dec. 23, 1986

[54] METHOD FOR INCORPORATING CHLORPYRIFOS INTO THERMOPLASTIC RESINS

[75] Inventors: Jiro Kozuma, Fujisawa; Hirohiko Hamaguchi, Yokohama; Tetsuya Shibahara, Yamato; Joseph P. Strasser, Tokyo, all of Japan

[73] Assignee: Dow Chemical Japan Limited, Tokyo, Japan

[21] Appl. No.: 698,779

[22] Filed: Feb. 6, 1985

[51] Int. Cl.$^4$ .................. A01N 17/10; A01N 17/08; A01N 25/10; C08K 5/52
[52] U.S. Cl. ......................................... 523/122; 424/78; 514/64; 514/89; 524/99; 524/297; 524/567
[58] Field of Search .................. 514/89, 64; 424/78; 523/122

[56] References Cited

U.S. PATENT DOCUMENTS

| | | | |
|---|---|---|---|
| 3,886,236 | 5/1975 | D'Alelio | 523/122 |
| 3,890,270 | 6/1975 | Minieri | 523/122 |
| 4,160,335 | 7/1979 | Kohorn | 424/84 |
| 4,435,383 | 3/1984 | Wysong | 424/78 |
| 4,528,125 | 7/1985 | Alderman et al. | 252/522 A |

FOREIGN PATENT DOCUMENTS 0121712 10/1984 European Pat. Off. .

Primary Examiner—Herbert J. Lilling
Attorney, Agent, or Firm—Joseph T. Majka; Ronald G. Brookens

[57] ABSTRACT

Novel composition and method for thermally stabilizing an O-pyridyl phosphate insecticide such as chlorpyrifos. The insecticide is mixed with a phthalate ester prior to its incorporation into a thermoplastic resin, such as polyvinyl chloride.

9 Claims, No Drawings

METHOD FOR INCORPORATING CHLORPYRIFOS INTO THERMOPLASTIC RESINS

BACKGROUND OF THE INVENTION

This invention relates to novel compositions and methods for thermally stabilizing O-pyridyl phosphate insecticides during its incorporation into thermoplastic resins.

Thermoplastic resins, polymers which can be softened and shaped by the application of heat and pressure and which return to their original condition when cooled to room temperature, are used in making articles such as underground pipelines and cables.

O-pyridyl phosphate insecticides have been incorporated into pipes and cables made from thermoplastic resins to make the resulting pipe or cable resistant to insect damage, particularly from ants and termites. Generally, in a known method for making insecticide-impregnated pipe, a thermoplastic resin, a stabilizer and a phthalate ester are kneaded together and then an O-pyridyl phosphate insecticide is incorporated therein. This resin containing the O-pyridyl phosphate insecticide is pelleted into beads or pellets which are later used to make the pipe.

However, a problem exists during the step of incorporation of the O-pyridyl phosphate insecticide into the resins as the O-pyridyl phosphates are thermally labile and unstable at the temperatures used for incorporation. At the temperatures of about 160° to about 200° C. used in the manufacture of plastic articles, the 0-pyridyl phosphates decompose, thereby preventing manufacturers from accurately and precisely metering the desired quantity of insecticide into the thermoplastic resin. The present invention overcomes this problem by providing a composition and a method for thermally stabilizing 0-pyridyl phosphate compounds during its incorporation into thermoplastic resins.

SUMMARY OF THE INVENTION

The present invention provides a composition comprising
(a) an O-pyridyl phosphate of the formula

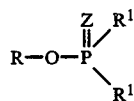

wherein
R represents halopyridyl,
Z is oxygen or sulfur, and each
$R^1$ is loweralkoxy, amine or loweramino; and
(b) a phthalate ester of the formula

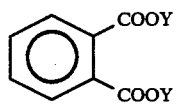

wherein
Y is alkyl from about 2 to about 20 carbon atoms or

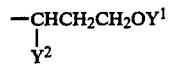

wherein
$Y^1$ is alkyl from 1 to about 20 carbon atoms and
$Y^2$ is hydrogen or methyl,
said O-pyridyl phosphate and said phthalate ester being present in proportions effective to prevent appreciable decomposition of said O-pyridyl phosphate upon heating said composition.

The present invention also provides a method for thermally stabilizing an O-pyridyl phosphate by (a) mixing the O-pyridyl phosphate with a phthalate ester as hereinbefore described and (b) incorporating the mixture into a thermoplastic resin. The resin containing the O-pyridyl phosphate can then be pelleted into beads, pellets, etc. used to make plastic articles which are resistant to insect damage.

DETAILED DESCRIPTION OF THE INVENTION

O-pyridyl phosphates, as defined hereinbefore, are known insecticide compounds. Methods for making these compounds are disclosed in U.S. Pat. No. 3,244,586 incorporated herein by reference. A preferred O-pyridyl phosphate is O,O-diethyl-3,5,6-trichloro-2-pyridyl phosphorothioate, commonly known as chlorpyrifos.

Phthalate esters, as defined hereinbefore, are known compounds and are used commercially as plasticizers for many resins and elastomers. Methods for making these compounds may be found in U.S. Pat. No. 3,064,046 and 3,088,974, incorporated herein by reference. A preferred phthalate ester is dioctyl phthalate.

The term "themoplastic resins" is used herein to include, but is not limited to resins of polystyrene, acrylonitrile, methacrylate ester or combinations thereof. A preferred thermoplastic resin is polyvinyl chloride (PVC). Thermoplastic resins are polymer materials well known to those skilled in the art. Stabilizers for thermoplastic resins are materials which prevent degradation of the resin exposed to environmental variation such as heat, sunlight and the like. Such stabilizers are known compounds to one skilled in the art.

The compositions of the present invention are prepared by mixing together an O-pyridyl phosphate insecticide with a phthalate ester in proportions effective to prevent appreciable decomposition of said O-pyridyl phosphate upon heating of the composition. Where the weight proportions of the phthalate ester to the total composition is from about 70 to about 99 percent or more, good thermal protection of the O-pyridyl phosphate ester is attained. The compositions of the present invention can be heated without the appreciable decomposition of the O-pyridyl phosphate that would otherwise occur upon heating of the O-pyridyl phosphate compound alone. It is contemplated the compositions of the present invention can be heated from temperatures of about 160° C. to about 200° C. and still provide good thermal protection of the O-pyridyl phosphate.

Methods for carrying out the present invention are performed by (a) mixing the O-pyridyl phosphate and the phthalate ester in proportions effective to prevent appreciable decomposition of the O-pyridyl phosphate upon heating of the mixture and (b) incorporating said mixture into a thermoplastic resin. Generally, the thermoplastic resin is heated to temperatures which soften or liquify the resin sufficiently to permit incorporation of the mixture containing the O-pyridyl phosphate into the resin. The proportions of the phthalate ester to the O-pyridyl phosphate are those hereinbefore described for the composition. A preferred O-pyridyl phosphate for performing the methods of the present invention is chlorpyrifos. A preferred phthalate ester is dioctyl phthalate. Thermoplastic resins which are suitable for performing the methods of the present invention include polystyrene, acrylonitrile, methacylate ester, polyethylene and combinations therof. A particularly preferred resin is polyvinyl chloride (PVC). The amount of O-pyridyl phosphate which may be incorporated into the plastic resin varies, depending in part upon the solubility of the O-pyridyl phosphate in the thermoplastic resin. Generally, the O-pyridyl phosphate is present in the resin in proportions ranging from about 0.01 to about 25 percent by weight, preferably about 1 to about 2 percent.

In another embodiment of the present invention, a thermoplastic resin, a stabilizer for the resin, and a phthalate ester as hereinbefore described, are kneaded together. The mixture of the O-pyridyl phosphate and the phthalate ester is further kneaded into the kneaded thermoplastic resin. The kneaded thermoplastic resin containing the O-pyridyl phosphate is then cooled and pelleted into beads, pellets or pieces used to manufacture plastic articles. The O-pyridyl phosphates, phthalate esters and thermoplastic resins are similar to those hereinabove described.

The following examples illustrate the present invention in a manner by which it can be practiced but, as such, should not be construed as limitations upon the overall scope of the same.

EXAMPLE 1

Predetermined amounts of technical grade chlorpyrifos and dioctyl phthalate were mixed to give solutions containing 0.0, 79.8, 90.1 and 95.0 percent by weight of dioctyl phthalate. Separate solutions were heated to temperatures of 140° C., 160° C., 180° C. or 200° C. for periods of zero (0), 30, 60 or 90 minutes (min). The solutions were analyzed for the amount of chlorpyrifos remaining in the solution. Results of the analysis are provided in Table 1.

TABLE 1

| Temperature | Proportion of Dioctyl Phthalate in Percent | Percent Chlorpyrifos Remaining After | | | |
|---|---|---|---|---|---|
| | | 0 Min. | 30 Min. | 60 Min. | 90 Min. |
| 200° C. | 0.0 | 100.0 | 80.9 | 53.6 | 25.4 |
| | 79.8 | 100.0 | 96.0 | 81.7 | 60.9 |
| | 90.1 | 100.0 | 96.1 | 90.1 | 86.1 |
| | 95.0 | 100.0 | 99.4 | 95.4 | 93.6 |
| 180° C. | 0.0 | 100.0 | 92.6 | 86.1 | 81.6 |
| | 79.8 | 100.0 | 95.5 | 95.0 | 89.0 |
| | 90.1 | 100.0 | 97.7 | 95.8 | 94.0 |
| | 95.0 | 100.0 | 99.4 | 98.0 | 95.8 |
| 160° C. | 0.0 | 100.0 | 99.5 | 95.9 | 92.7 |
| | 95.0 | 100.0 | 99.2 | 98.6 | 96.0 |
| 140° C. | 0.0 | 100.0 | 100.0 | 99.7 | 99.5 |
| | 95.0 | 100.0 | 100.0 | 99.6 | 99.6 |

EXAMPLE 2

Predetermined amounts of polyvinyl chloride resin, a stabilizer and dioctylphthalate were kneaded together at a temperature of 200° C. A test group of pellets were prepared by further kneading a solution containing chlorpyrifos and dioctylphthalate into the resin mixture in amounts calculated to bring the concentration of chlorpyrifos in the resin to 1.0 and 2.0 percent by weight. The resin was subsequently pelleted. A second group of pellets as controls were similarly prepared but without the use of dioctylphthalate. Chlorpyrifos used was taken from a formulation of Lentrek ® 40EC termiticide, trademark of The Dow Chemical Company, Midland, Mich. Lentrek ® 40EC termiticide is a formulation of about 43 percent chlorpyrifos and about 57 percent inert ingredients based on a weight basis. After pelleting, the final concentration of chlorpyrifos remaining in the pellets was determined and are presented in Table 2.

TABLE 2

| | Thermal Stability of Chloropyrifos in Polyvinyl Chloride (PVC) | |
|---|---|---|
| Calculated Percent Concentration of Chlorpyrifos in PVC Immediately After Addition | Percent Concentration of Chlorpyrifos Found in PVC Without Use of Dioctyl Phthalate | Percent Concentration of Chlorpyrifos Found in PVC With the Use of Dioctyl Phthalate |
| 1.0 | 0.76 | 0.98 |
| 2.0 | 1.55 | 1.98 |

What is claimed is:

1. A method for thermally stabilizing an O-pyridyl phosphate compound of the formula

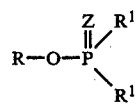

wherein
R represents halopyridyl,
Z is oxygen or sulphur, and
each $R^1$ is loweralkyoxy, amino or loweralkylamino, comprising
(a) mixing said O-pyridyl phosphate with a phthalate ester of the formula

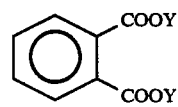

wherein
Y is alkyl from about 2 to about 20 carbon atoms
or

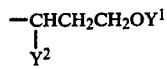

wherein
Y$^1$ is alkyl from about 1 to about 20 carbon atoms, and
Y$^2$ is hydrogen or methyl;
said O-pyridyl phosphate and said phthalate ester being present in proportions effective to prevent appreciable ecomposition of said O-pyridyl phosphate upon heating said mixture, and
(b) incorporating said mixture into a thermoplastic resin heated to a temperature which would decompose the O-pyridyl phosphate compound if the O-pyridyl phosphate were heated alone.

2. The method of claim 1 wherein said O-pyridyl phosphate is chlorpyrifos.

3. The method of claim 1 wherein said phthalate ester is dioctyl phthalate.

4. The method of claim 1 wherein said O-pyridyl phosphate is chlorpyrifos and said phthalate ester is dioctyl phthalate.

5. The method of claim 1 wherein said thermoplastic resin is selected from the group consisting of polyvinyl chloride, polystyrene, acrylonitrile, methacrylate ester, polyethylene and combinations thereof.

6. The method of claim 1 wherein said thermoplastic resin is polyvinyl chloride.

7. The method of claim 1 wherein said O-pyridyl phosphate is chlorpyrifos, said phthalate ester is dioctyl phthalate and said thermoplastic resin is polyvinyl chloride.

8. The method of claim 1 wherein said steps of mixing and incorporating are performed by kneading.

9. The method of claim 1 further comprising (c) pelleting the resin containing said O-pyridyl phosphate.

* * * * *

UNITED STATES PATENT AND TRADEMARK OFFICE
CERTIFICATE OF CORRECTION

PATENT NO. : 4,631,301

DATED : Dec. 23, 1986

INVENTOR(S) : Jiro Kozuma, Hirohiko Hamaguchi, Tetsuya Shibahara and Joseph P. Strasser It is certified that error appears in the above-identified patent and that said Letters Patent is hereby corrected as shown below:

Col. 2, line 37, ""themoplastic" should read -- "thermoplastic--

Col. 3, line 11, "methacylate" should read -- methacrylate --;
line 12, "therof" should read --thereof --

Col. 4, line 59, "loweralkyoxy" should read -- loweralkoxy --

Col. 5, line 16, "ecomposition" should read -- decomposition --

Signed and Sealed this

Eighteenth Day of August, 1987

*Attest:*

DONALD J. QUIGG

*Attesting Officer*  *Commissioner of Patents and Trademarks*